(12) United States Patent
Albert et al.

(10) Patent No.: US 7,727,260 B2
(45) Date of Patent: Jun. 1, 2010

(54) METHOD AND APPARATUS FOR BONE STABILIZATION

(75) Inventors: Todd James Albert, Narberth, PA (US); Rafail Zubok, Midland Park, NJ (US); Mikhail Kvitnitsky, Clifton, NJ (US)

(73) Assignee: Accelerated Innovation, LLC, Clifton, NJ (US)

( * ) Notice: Subject to any disclaimer, the term of this patent is extended or adjusted under 35 U.S.C. 154(b) by 601 days.

(21) Appl. No.: 11/385,083

(22) Filed: Mar. 21, 2006

(65) Prior Publication Data

US 2006/0217719 A1 Sep. 28, 2006

Related U.S. Application Data

(60) Provisional application No. 60/665,010, filed on Mar. 24, 2005.

(51) Int. Cl.
*A61B 17/70* (2006.01)

(52) U.S. Cl. .............. 606/259; 606/260; 606/261; 606/264; 606/99; 606/104

(58) Field of Classification Search .............. 606/60, 606/246–279, 99, 104
See application file for complete search history.

(56) References Cited

U.S. PATENT DOCUMENTS

| | | | |
|---|---|---|---|
| 4,648,388 A | | 3/1987 | Steffee |
| 5,171,279 A | | 12/1992 | Mathews |
| 5,261,913 A | * | 11/1993 | Marnay ............... 606/251 |
| 5,437,669 A | * | 8/1995 | Yuan et al. ........... 606/278 |
| 5,562,660 A | | 10/1996 | Grob |
| 5,569,248 A | | 10/1996 | Mathews |
| 5,607,425 A | | 3/1997 | Rogozinski |
| 5,728,097 A | | 3/1998 | Mathews |
| 5,810,815 A | * | 9/1998 | Morales ............... 606/250 |
| 6,235,028 B1 | | 5/2001 | Brumfield et al. |
| 6,530,929 B1 | | 3/2003 | Justis et al. |
| 6,793,656 B1 | | 9/2004 | Mathews |
| 6,899,714 B2 | * | 5/2005 | Vaughan .............. 606/86 A |
| 7,008,422 B2 | | 3/2006 | Foley et al. |
| 7,011,660 B2 | | 3/2006 | Sherman et al. |
| 7,250,052 B2 | * | 7/2007 | Landry et al. ........ 606/86 A |
| 2002/0143329 A1 | * | 10/2002 | Serhan et al. .......... 606/61 |

(Continued)

OTHER PUBLICATIONS

International Preliminary Report on Patentability and Written Opinion for International Application PCT/US2006/10109.

(Continued)

*Primary Examiner*—Thomas C Barrett
*Assistant Examiner*—Andrew Yang
(74) *Attorney, Agent, or Firm*—Matthew B. Dernier, Esq.; Gibson & Dernier LLP

(57) ABSTRACT

A stabilization system for implantation in a patient includes: at least first and second bone anchors, each bone anchor including a shaft extending in a respective bone insertion direction for connection to a respective bone of a patient, and a fastening member; and an elongate member comprising a first end portion, a first transverse portion extending transversely from the first end portion, a second end portion, a second transverse portion extending transversely from the second end portion, and a connecting portion extending in a longitudinal direction between the first and second transverse portions.

67 Claims, 12 Drawing Sheets

U.S. PATENT DOCUMENTS

| | | |
|---|---|---|
| 2002/0161368 A1 | 10/2002 | Foley et al. |
| 2003/0236447 A1* | 12/2003 | Ritland ................. 600/210 |
| 2004/0138662 A1 | 7/2004 | Landry et al. |
| 2004/0143265 A1 | 7/2004 | Landry et al. |
| 2004/0172022 A1 | 9/2004 | Landry et al. |
| 2005/0033434 A1 | 2/2005 | Berry |
| 2005/0065517 A1 | 3/2005 | Chin |
| 2005/0070901 A1 | 3/2005 | David |
| 2005/0070917 A1 | 3/2005 | Justis |
| 2005/0075644 A1 | 4/2005 | DiPoto et al. |
| 2006/0084993 A1 | 4/2006 | Landry et al. |
| 2008/0051787 A1* | 2/2008 | Remington et al. ........... 606/61 |

OTHER PUBLICATIONS

International Search Report and Written Opinion for International Application PCT/US2006/10109.

* cited by examiner

METHOD AND APPARATUS FOR BONE STABILIZATION

CROSS REFERENCE TO RELATED APPLICATIONS

This application claims the benefit of U.S. Provisional Patent Application No. 60/665,010, filed Mar. 24, 2005, the entire disclosure of which is hereby incorporated by reference.

BACKGROUND OF THE INVENTION

The present invention is directed to vertebral stabilization of a spine using one or more rods anchored into the vertebrae.

Back pain is one of the most common and often debilitating conditions affecting millions of people in all walks of life. Today, it is estimated that over ten million people in the United States alone suffer from persistent back pain. Approximately half of those suffering from persistent back pain are afflicted with chronic disabling pain, which seriously compromises a person's quality of life and is the second most common cause of worker absenteeism. Further, the cost of treating chronic back pain is very high, even though the majority of sufferers do not receive treatment due to health risks, limited treatment options and inadequate therapeutic results. Thus, chronic back pain has a significantly adverse effect on a person's quality of life, on industrial productivity, and on heath care expenditures.

Degenerative spinal column diseases, such as disc degenerative diseases (DDD), spinal stenosis, spondylolisthesis, and so on, need surgical operation if they do not respond to conservative treatment.

Various methods of spinal immobilization have been known and used during this century in the treatment of spinal instability and displacement. One treatment for spinal stabilization is immobilization of the joint by surgical fusion, or arthrodesis. This method has been known since its development in 1911 by Hibbs and Albee. However, in many cases, and in particular, in cases involving fusion across the lumbosacral articulation and when there are many levels involved, pseudoarthrosis is a problem. It was discovered that immediate immobilization was necessary in order to allow a bony union to form.

Typically, spinal decompression is the first surgical procedure that is performed. The primary purpose of decompression is to reduce pressure in the spinal canal and on nerve roots located therein by removing a certain tissue of the spinal column to reduce or eliminate the pressure and pain caused by the pressure. If the tissue of the spinal column is removed the pain is reduced but the spinal column is weakened. Therefore, fusion surgery (e.g., ALIF, PLIF or posterolateral fusion) is often necessary for spinal stability following the decompression procedure. However, following the surgical procedure, fusion takes additional time to achieve maximum stability and a spinal fixation device is typically used to support the spinal column until a desired level of fusion is achieved. Depending on a patient's particular circumstances and condition, a spinal fixation surgery can sometimes be performed immediately following decompression, without performing the fusion procedure. The fixation surgery is performed in most cases because it provides immediate postoperative stability and, if fusion surgery has also been performed, it provides support of the spine until sufficient fusion and stability has been achieved.

Internal fixation refers to therapeutic methods of stabilization which are wholly internal to the patient. External fixation in contrast involves at least some portion of the stabilization device which is external to the patient's body. Internal fixation is advantageous since the patient is allowed greater freedom with the elimination of the external portion of the device and the possibility of infections, such as pin tract infection, is reduced.

Conventional methods and apparatus for vertebral stabilization and/or fusion involve fixing a rod between adjacent vertebrae to prevent motion therebetween. Usually, more than one rod is utilized in a posterior, bilateral configuration with respect to the spinous process. Respective pedicle screws are inserted into the pedicles of the vertebrae through the facets thereof such that the tulips of the screws may fuse to the vertebrae. A rod is fixed to a pair of tulips in order to fix the relative motion between the adjacent vertebrae. Multi-level fusion may be achieved by utilizing more than two pedicle screws on each side of the spinous process and fixing a rod to all of the respective screws. The surgery may require an incision of approximately 60-80 mm longitudinally along the posterior of the spine and peeling back the muscle on each side of the spinous process to expose the facets and pedicles of the adjacent vertebrae.

This surgery is significantly invasive because it involves trauma to the skin, fat, and particularly the muscle. As it requires a significant period of time to heal the muscle and achieve at least partial elasticity thereof, in at least some patients it is not desirable to traumatize muscle.

Other techniques have been developed to reduce the trauma to the muscle during surgery as described in U.S. Pat. No. 6,530,929 and U.S. patent application No. 2002/0161368, the entire disclosures of which are hereby incorporated by reference in their entirety. These publications disclose making three "stub incisions" on each side of the spinous process to accommodate insertion of a rod/pedicle screw assembly. The first and second stub incisions are made adjacent to the respective vertebrae and the third incision is made longitudinally offset from the other two incisions. Each incision is dilated and respective tubes are inserted into the incisions such that they extend from the skin through the muscle to the respective pedicles of the adjacent vertebrae. Screws are then passed through the tubes and inserted into the respective pedicles. A special instrument is then utilized to shape the rod. The instrument is also utilized to insert the rod through the third incision and navigate the rod longitudinally through the muscle from the third incision to the second and first incisions such that the rod passes through respective tulips of each screw. The rod may then be fixed to the respective screws.

While this technique reduces the trauma to the skin and muscle as compared with the aforementioned surgical technique, it still results in a significant amount of trauma to the muscle as the rod is forced through and along the muscle when traveling from the third incision to each of the second and first incisions.

Therefore, conventional spinal fixation devices and surgical techniques have not provided a satisfactory solution to the problems associated with spinal fixation surgery, particularly with respect to minimizing muscle trauma and the size, length and number of surgical incisions required.

SUMMARY OF THE INVENTION

In accordance with one or more embodiments of the present invention, a stabilization system for implantation in a patient includes: at least first and second bone anchors, each bone anchor including a shaft extending in a respective bone insertion direction for connection to a respective bone of a patient, and a fastening member; and an elongate member comprising a first end portion, a first transverse portion extending transversely from the first end portion, a second end portion, a second transverse portion extending transversely from the second end portion, and a connecting portion extending in a longitudinal direction between the first and second transverse portions. The respective fastening members are operable to receive and fix the first and second end portions in respective receiving directions, which are transverse to the longitudinal and bone insertion directions.

The first and second transverse portions may be operable to position the connecting portion superfascially with respect to muscle tissue of the patient. Alternatively of additionally, the first and second transverse portions may be operable to position the connecting portion, when implanted, a predetermined distance away from the fastening members of the bone anchors. Alternatively of additionally, the predetermined distance is about a thickness of muscle tissue proximate to the bone anchors. For example, the muscle tissue of the patient may be posterior to the patient's spine. Alternatively of additionally, the first and second transverse portions are operable to offset the connecting portion with respect to the fastening members in a direction at least partially opposite the respective bone insertion directions.

In accordance with one or more further embodiments of the present invention, a multi-level stabilization system for implantation in a patient includes: at least first, second and third bone anchors, each bone anchor including a shaft extending in a respective bone insertion direction for connection to a respective bone of a patient, and a fastening member; and an elongate member comprising a first end portion, a first transverse portion extending transversely from the first end portion, a second end portion, a second transverse portion extending transversely from the second end portion, a third end portion and a third transverse portion extending transversely from the third end portion, and a connecting portion extending in a longitudinal direction to each of the first, second, and third transverse portions. The respective fastening members may be operable to receive and fix the first, second, and third end portions in respective receiving directions, which are transverse to the longitudinal and bone insertion directions.

The stabilization system may further include a coupling for interconnecting the third transverse portion to the connecting portion. Preferably, the third transverse portion is disposed between the first and second transverse portions.

In accordance with one or more further embodiments of the present invention, a stabilization system for implantation in a patient includes: at least first and second bone anchors, each bone anchor including a shaft extending in a respective bone insertion direction for connection to a respective bone of a patient, and a fastening member; and an elongate member comprising first and second end portions, each extending in respective insertion directions, and a connecting portion extending in a longitudinal direction transverse to the respective insertion directions. The respective fastening members may be operable to receive and fix the first and second end portions in the respective insertion directions, which are transverse to the longitudinal and bone insertion directions.

In accordance with one or more further embodiments of the present invention, an access sleeve for use in implanting a stabilization system into a patient, comprising: an exterior surface; first and second spaced apart ends, the second end being operatively connectable to a rod fastening member of a bone anchors; an interior surface defining a volume; a slot extending at least partially along a length of the exterior surface of the access sleeve and providing an opening into the volume; and a channel extending along a length of the interior surface, being disposed substantially opposite to the slot, and including a contour complementing a contour of an end of an interconnecting rod.

In accordance with one or more further embodiments of the present invention, a method of implanting a bone stabilization system into a patient includes: making first and second incisions through tissue of the patient to bone structure to be stabilized; making a third incision connecting the first and second incisions, the third incision not extending substantially through muscle of the patient; inserting first and second bone anchors into the first and second incisions, respectively, and fixing them to the bone structure; and inserting an elongate member through the incisions such that first and second ends thereof are received into and fixed to respective fastening members of the bone anchors, and such that a connecting portion of the elongate member is superfascial to the muscle tissue of the patient.

In accordance with one or more further embodiments of the present invention, a method of implanting a bone stabilization system into a patient includes: making at least one incision through tissue of the patient and exposing bone structure to be stabilized; and inserting first and second bone anchors into the at least one incision and fixing them to the bone structure in respective bone insertion directions such that respective receiving directions for receiving an elongate member therebetween are transverse to a longitudinal direction of the elongate member and the bone insertion directions.

Other aspects, features, advantages, etc. will become apparent to one skilled in the art when the description of the preferred embodiments of the invention herein is taken in conjunction with the accompanying drawings.

BRIEF DESCRIPTION OF THE DRAWINGS

For the purposes of illustrating the various aspects of the invention, there are shown in the drawings forms that are presently preferred, it being understood, however, that the invention is not limited to the precise arrangements and instrumentalities shown.

DETAILED DESCRIPTION

Figure 1:
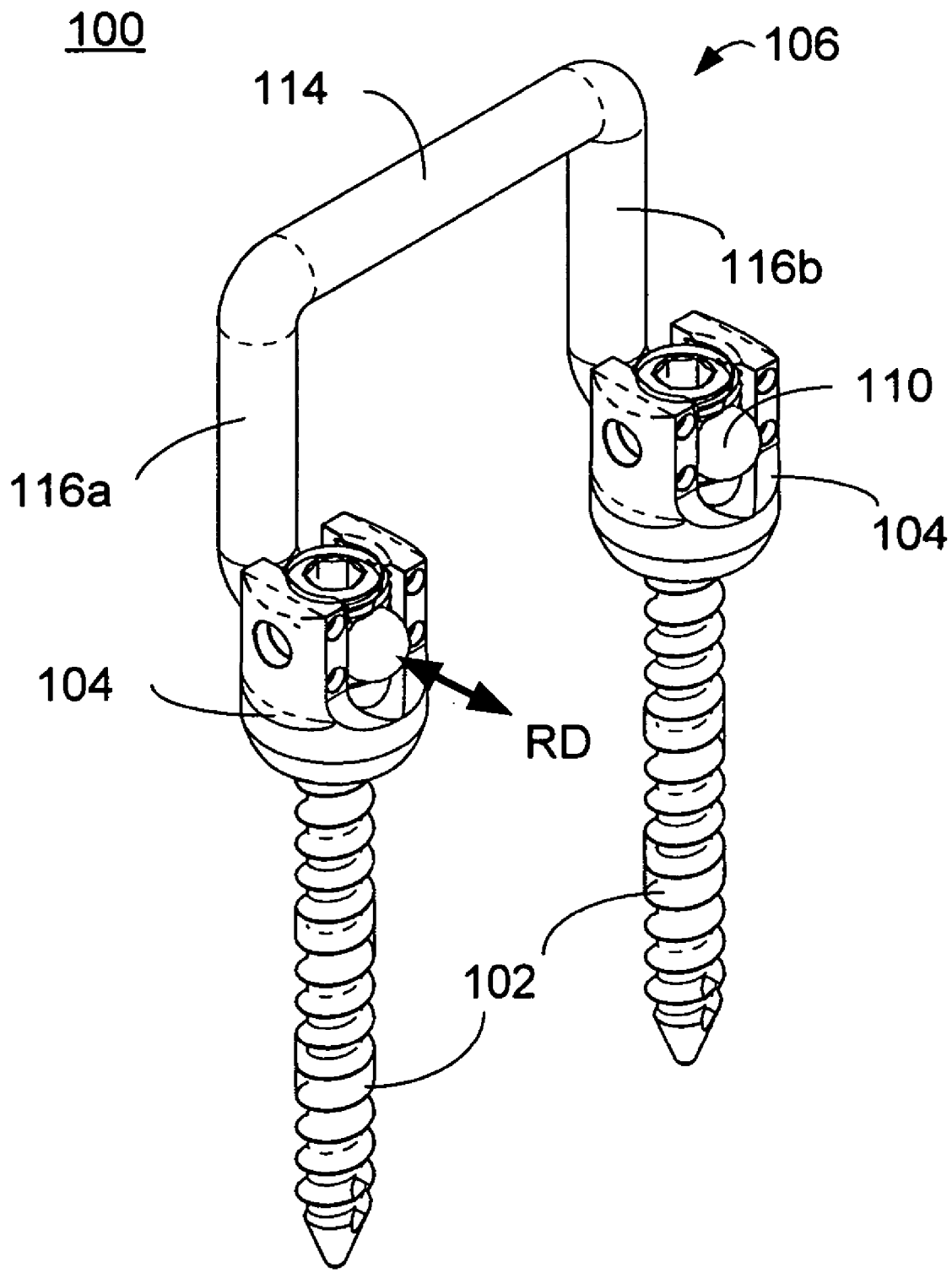
FIG. 1 is a perspective view of a bone stabilizer system in accordance with one or more embodiments of the present invention.

With reference to the drawings, wherein like numerals indicate like elements, there is shown in FIG. 1 an embodiment of a stabilization system 100 in accordance with one or more aspects of the present invention. Although it is contemplated that the stabilization system 100 may be used for internal fixation of respective bones of a patient, such as vertebrae of the spine, other bone stabilization applications are considered within the scope of the invention. For the purposes of discussion, the examples herein are directed to using the system 100 for stabilization of vertebral bones of a spine.

The stabilization system 100 includes bone anchors 102 (such as pedicle screws), and an elongate, interconnecting rod 106. Each bone anchor 102 preferably includes a head (not shown), a shaft (for insertion and fixation to bone), and a fastening member 104, such as a tulip. In a preferred embodiment, the fastening member 104 is operable to receive the head and to achieve various articulation positions with respect to the shaft of the bone anchor 102. (It is noted that monolithic bone anchors are also contemplated, although they may not permit articulation of the fastening member.) The fastening members 104 are operable to receive respective end portions 110 of the rod 106 and fix them to the bone anchors 102 when a desirable articulation is achieved. Those skilled in the art will appreciate that any of the known pedicle screw/tulip systems (whether multi-piece or monolithic) may be employed so long as they are consistent with the objectives and functions discussed above and herein below.

Figure 2:
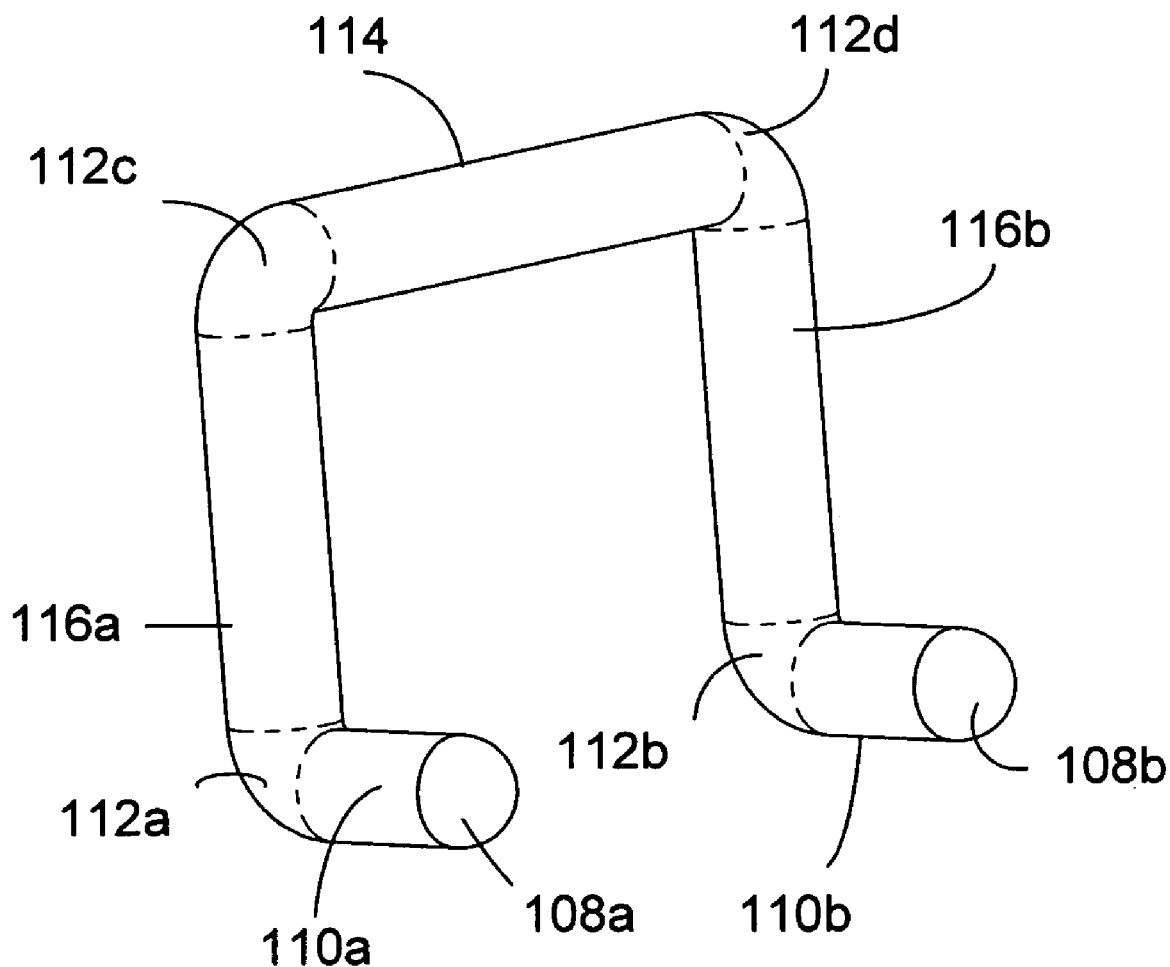
FIG. 2 is a perspective view of a rod suitable for use with the bone stabilizer system of FIG. 1 and/or one or more other embodiments of the present invention.

FIG. 2 is a perspective view of one embodiment of the rod 106. The rod 106 may be substantially U-shaped and is preferably pre-formed prior to surgery. Notably, the rod 106 includes end portions 110a, 110b, a longitudinal connection portion 114, and a pair of offset transverse portions 116a, 116b. The end portions 110a, 110b extend transversely from the respective transverse portions 116a, 116b by way of joints 112a, 112b, respectively. The transverse portions 116a, 116b extend transversely from the connection portion 114 to the respective end portions 110a, 110b, respectively, by way of joints 112c, 112d. By way of example as illustrated in FIGS. 1 and 2, the respective bone anchors 102 in system 100 lay substantially in a first plane. The orientation of the end portions 110a, 110b of the rod 106 and the orientation of the receiving directions of the fastening members 104 are operable to position the connecting portion 114 in a laterally offset position from the first plane. The joints 112a-d may be formed by bending the rod 106, which may be done either prior to or during the surgical implantation procedure. As some embodiments of the rod 106 may dictate that the rod 106 be of substantial stiffness, formation of the joints 112a-d during the surgical procedure (and/or outside the manufacturing process) might be difficult.

The respective end portions 110a, 110b of the rod 106 include terminal ends 108a, 108b. Notably, the end portions 110a, 110b are aligned substantially parallel to each other and lie in a plane that is transverse to a plane in which the two transverse portions 116a, 116b lie. The alignment of the end portions 110a, 110b is thus particularly suited to the situation in which the fastening members 104 of the stabilization system 100 are oriented to accept the end portions 110a, 110b so aligned. In other words, the fastening members 104 may include respective channels, bores, etc. oriented essentially parallel to each other and transverse to the longitudinal direction of the connecting portion 114 of the rod 106. In various embodiments, the fastening member 104 of each bone anchor 102 provides a "receiving direction" into which the end portion 110 of the rod 106 is received, and/or by which the orientation of the end portion 110 of the rod 106 is determined. For example, in FIG. 1, the receiving direction RD is dictated by the orientation of the channel of the fastening member 104.

Although it is desirable for the implanted fastening members 104 to provide a receiving direction in precise alignment, depending on the type of rod 106 used, it is understood that in practice the actual receiving direction provided by the implanted fastening members 104 may not conform exactly to the relatively symmetric orientation of the rod end portions 110. Thus, adjustments in the articulation of the fastening members 104 and/or the shape of the rod 106 may be made before or during the surgical process, as described below. For example, the orientation of the transverse portions 116a, 116b and/or the end portions 110a, 110b may be altered to conform with the receiving directions provided by the implanted fastening members 104.

When the implanted fastening members 104 are positioned as illustrated in FIG. 1, the orientation of the end portions 110a, 110b allow for each of the transverse portions 116a, 116b to extend from their respective end portion 110a, 110b in a direction substantially opposite the bone insertion direction, to the connecting portion 114. The phrase "substantially opposite the bone insertion direction" is intended to include the situation in which respective axes of the transverse portions 116a, 116b, extending away from the respective end portions 110a, 110b, have a significant vector component in a direction opposite the bone insertion direction. It is noted that, in practice, the directions used to describe the receiving directions, rod portions and other aspects of the invention having directionally relevant descriptions are not meant to be exact, but may vary somewhat, as those of ordinary skill in the orthopedic arts implicitly understand and appreciate.

As will be discussed in greater detail below, the orientation and direction of the transverse portions 116a, 116b permit the connecting portion 114 to reside superfascially. The connecting portion 114 may overlie muscle tissue of the patient, such as the smooth muscle tissue overlaying the vertebral bodies of the spine. This may advantageously result in less muscle trauma for the patient.

Figure 3:
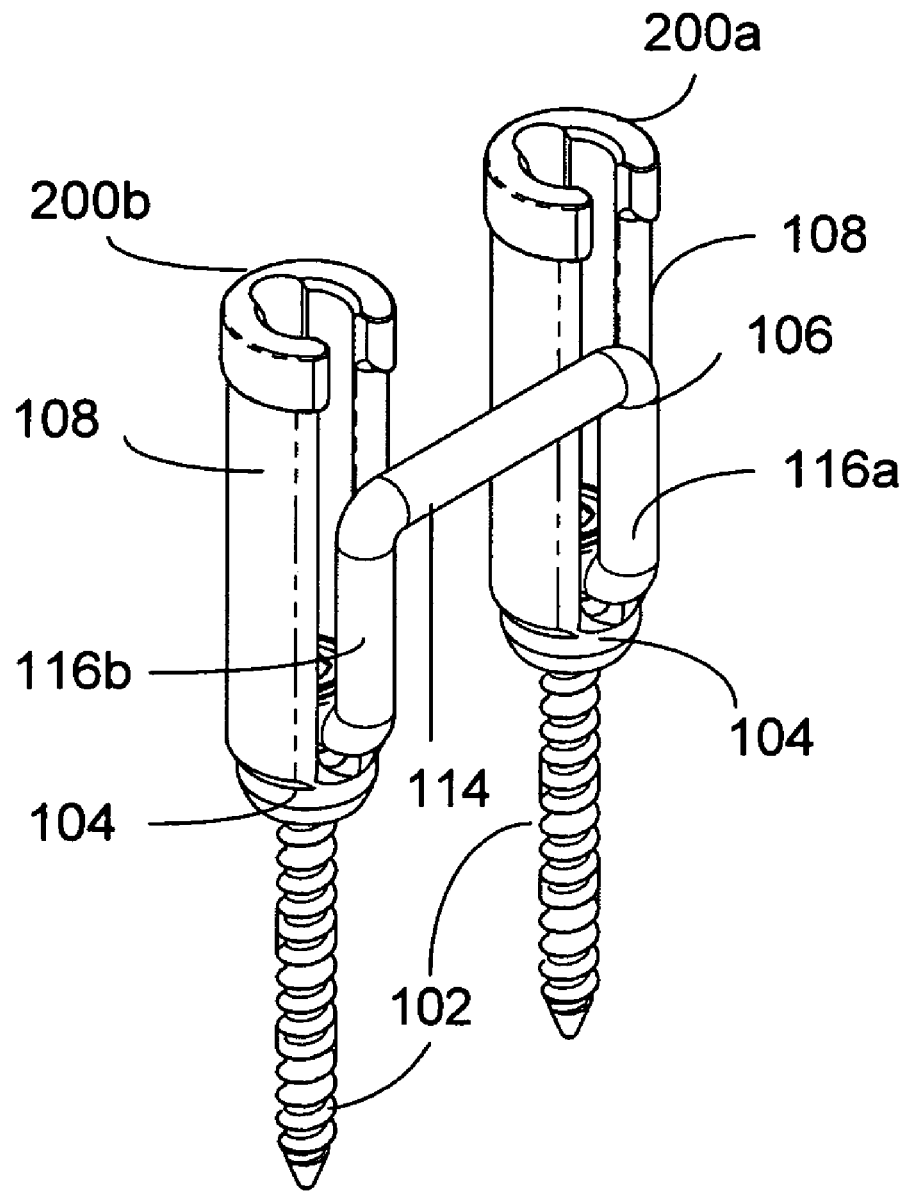
FIG. 3 is a perspective view of a the bone stabilizer system of FIG. 1 including implantation apparatus in accordance with one or more embodiments of the present invention.
Figure 4A:
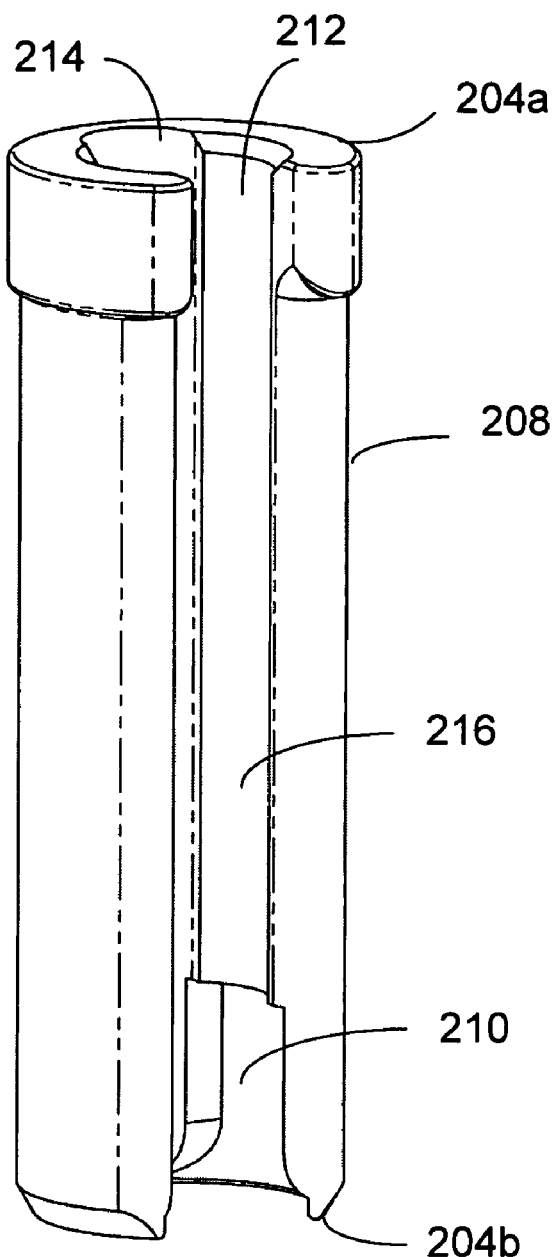
FIGS. 4a-4b are perspective and top views, respectively, of a sleeve of the bone stabilizer system of FIG. 3.
Figure 4B:
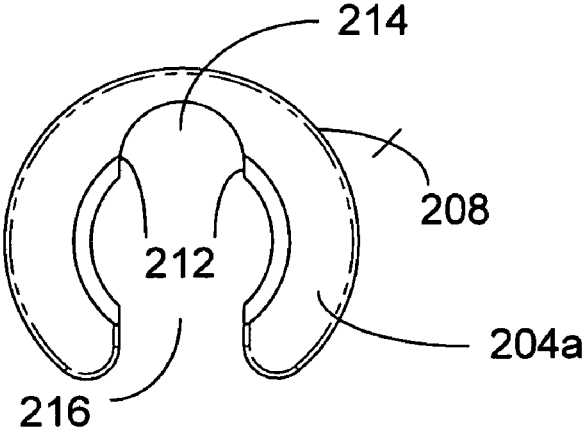

Reference is now made to FIGS. 3 and 4a-b, which illustrate further alternative details of the invention. FIG. 3 is a perspective view of the stabilization system 100 of FIG. 1 with optional access sleeves 200a, 200b for assisting in the implantation process. FIGS. 4a-b illustrate specific details of the sleeves 200. In general, the sleeves 200 are operable to removably engage the fastening members 104 of the bone anchors 102 and are used to assist in implanting the system 100 into a patient. Preferably, each sleeve 200 is of a generally cylindrical configuration and extends in a longitudinal direction. In one or more embodiments, the sleeves 200 may include an engagement portion 210 for removably engaging the fastening members 104. The engagement portion 210 may be sized and shaped to clamp to the given fastening member 104 by way of a friction fit and/or other clamping means. It is noted that the engagement portion 210 preferably includes structure, such as undercuts and/or other surfaces to engage the fastening member 104 in a clamping fashion. In the embodiment illustrated, the engagement portion 210 includes oppositely disposed cut-outs to receive the structures of the fastening member 104. Preferably, the sleeves 200 are somewhat resilient such that they may be press fit onto the bone anchors 102 and later pulled off with moderate force. The resiliency of the sleeves 200 may be achieved by forming same from a suitable polymer material. In a preferred embodiment, the sleeves 200 are pre-assembled to the bone anchors 102 and packaged (with or without the rod 106) in a sanitary manner for the surgeon.

Each sleeve 200 may also include a slot 216 and a channel 214 that extend from one end 204a to another end 204b of the sleeve 200. In some embodiments, the slot 216 and channel 214 need not extend all the way to ends 204a and/or 204b. As shown in FIG. 3, the respective slots 216 are preferably operable to permit the end portions 110a, 110b of the rod 106 to pass therethrough such that the sleeves 200 may assist in guiding the rod 106 into position for fixing to the bone anchors 102. The slot 216 is also in communication with the second end 204b of the sleeve 200 such that the sleeves 200 may be removed from the patient without disturbing the position of the rod 106 with respect to the bone anchors 102. As will be discussed in more detail below, the surgeon may remove the sleeves 200 after implantation, leaving the system 100 in place.

In one or more embodiments of the present invention, the channel 214 may be contoured to conform to the terminal end 108 of the rod 106. In the course of a surgical procedure to implant the stabilization system 100, once the sleeves 200 are in place and the bone anchors 102 are in place, a surgeon can use the slot 216 and channel 214 to assist in placing the rod 106 into position to span the space between the fastening members 104. This may be accomplished by placing one end 110a of the rod 106 into the slot 216 and channel 214 at the first end 204a of one of the sleeves 200a, and the other end 110b of the rod 106 into the slot 216 and channel 214 at the first end 204a of the other sleeve 200b. Thereafter, the surgeon may slide the rod 106 so the ends 110a, 110b of the rod 106 move from the first ends 204a of the sleeves 200 to the second ends 204b thereof. The slots 216 and/or channels 214 may thereby function as guiding support structures for the surgeon in guiding the rod 106 into its ultimate position. This will be discussed in more detail below.

By way of example, a procedure will now be described for implanting the stabilization system 100 in a patient for vertebral stabilization using the sleeves 200a, 200b. (Again, it is understood that the stabilization system 100 may be used in other application besides vertebral stabilization.) A respective stub incision is made over each of the vertebrae to be interconnected by the system 100. The "stub" incisions are relatively short in length and longitudinally disposed with respect to the spine of the patient. The stub incisions may be dilated if necessary. Next the surgeon may locate and drill holes into the respective vertebrae to receive the respective bone anchors 102.

Next, the respective sleeves 200a, 200b are engaged with the fastening members 104 of the bone anchors 102 via the engagement portion 210 (which may have been done pre-surgery and packaged in a sterile container). The shafts of the bone anchors 102 are then inserted into the respective stub incisions to the respective holes. At this point, the shafts of the bone anchors 102 may extend at or above the skin, with the sleeves 200 extending above the bone anchors 102. The surgeon may then insert an appropriate driver tool through the opening in the first end 204a of a given sleeve 200 to the head of the bone anchor 102 to drive the bone anchor 102 into the hole in the bone. As the bone anchor 102 is driven into the hole, the second end 204b of the sleeve 200 will enter the stub incision to a depth at which the surgeon has determined is appropriate for the fastening member 104. This procedure is repeated for each bone anchor 102. At this point, the respective sleeves 200a, 200b may extend above the skin of the patient and provide access to the fastening members 104.

The sleeves 200 are placed with their respective slots 216 oriented to match the orientation of the end portions 110a, 110b of the particular rod 106 that is employed. For example, the respective slots 216 of the access sleeves 200 are not directed toward one another; rather, they are oriented such that respective receiving directions thereof are substantially parallel to one another. Notably, the orientation of the slots 216 may also align the receiving directions of the fastening members 104 (the tulips) so that end portions 100a, 100b may be connected thereto. This is a desirable feature as the surgeon may not easily see into the incisions to align the receiving directions. Next, the respective bone anchors 102 are fixed to the respective vertebrae, and the fastening members 104, if articulable, are articulated to an orientation providing receiving directions oriented to match the orientation of the end portions 110a, 110b of the rod 106.

Before or after the sleeves 200 and bone anchors 102 are inserted into the stub incisions, the skin is preferably incised between the respective stub incisions (i.e., longitudinally along the spine and laterally offset from the spinous process). The skin and fat layers are preferably peeled back to expose the muscle; however, the muscle need not be disturbed other than by the stub incisions.

The surgeon may utilize one or more trials (not shown) to measure from the bottom of the respective fastening member 104 to the top of the muscle in order to ascertain a desirable length of the respective transverse portions 116a, 116b of the rod 106. The surgeon may also measure a distance between the respective stub incisions and/or fastening members 104 in order to ascertain a desirable length of the connection portion 114 of the rod 106. As the anatomy of the patient is likely not to result in perfect symmetry in alignment of the bone anchors 102, fastening members 104, sleeves 200, etc., the surgeon may adjust the orientation of the pre-formed rod 106 as needed. Alternatively, a surgeon may bend the rod 106 into the general configuration shown in FIG. 1 at the time of surgery. It is preferred, however, that the surgeon has a number of rods 106 available to him, where each rod 106 is of slightly different dimensions while still of the general U-shape configuration. The ends 110a, 110b of the rod 106 are then preferably inserted through the sleeves 200a, 200b to the respective fastening members 104. As noted above, relatively minor adjustments in the shape of the rod 106 may be made during the surgical process, such as extending the distance between respective end portions 110a, 110b, or the alignment thereof, etc.

In an actual surgery, the anatomy of the patient may cause the sleeves 200a, 200b to be somewhat anti-parallel (but generally directed away from the bone insertion directions). In one or more embodiments, the surgeon may use the slots 216 and/or channels 214 of the sleeves to assist in aligning the sleeves (and fastening members 104) to more easily receive the rod 106. The surgeon may insert the first end portion 110a of the rod 106 through the slot 116 of the first sleeve 200a such that the end portion 110a enters and slides in the channel 214 of the sleeve 200a along its length toward the fastening member 104 of the bone anchor 102. Then the surgeon may insert the second end portion 110b of the rod 106 through the slot 216 of the second sleeve 200b such that the second end portion 110b may enter and slide in the channel 214 of the second sleeve 2000b along its length toward the fastening member 104 of the bone anchor 102.

The insertion of the first and second end portions 110a, 110b of the rod 106 into the sleeve 200a, 200b thus urges the fastening members 104 into articulation positions suitable for receiving and fixing the rod 106 thereto. The surgeon may slide the rod along the slots 216 toward the fastening members 104 of the bone anchors 102, and fix the first and second end portions 110a, 110b thereof to the respective fastening members 104. As best seen in FIG. 3, the surgeon may remove a set screw of the fastening member 104 to permit access to the channel thereof from a vertical direction, which permits the end portions 110a, 110b of the rod 106 to be received in the fastening members 104. The surgeon may then place the set screws into the fastening members 104 and tighten same to fix the rod 106 to the bone anchors 102.

In general, the first and second transverse portions 116a, 116b are operable to offset the connecting portion 114 with respect to the fastening members 104 in a direction at least partially opposite the respective bone insertion directions. For example, the transverse portions 116a, 116b of the rod 106 may permit the connection portion 114 to lay superfascially adjacent to the muscle and extend longitudinally with respect to the spine without disturbing the muscle. Alternatively, the first and second transverse portions 116a, 116b are operable to position the connecting portion 114, when implanted, a predetermined distance away from the fastening members 104 of the bone anchors 102. The predetermined distance may be about the thickness of the muscle tissue proximate to the bone anchors 102. In the case of a posterior vertebral stabilization, the muscle tissue of the patient is posterior to the patient's spine.

Figure 5:
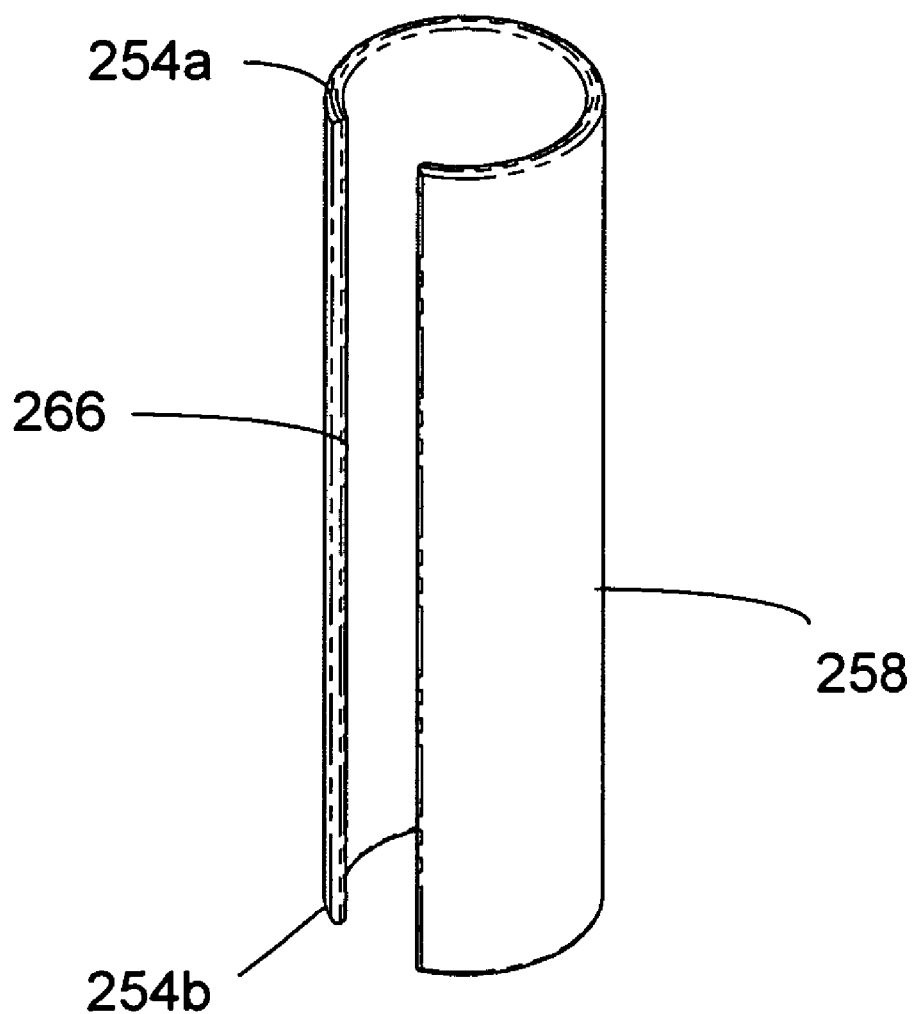
FIG. 5 is a perspective view of an alternative sleeve embodiment suitable for use with the stabilizer system of FIG. 1 and/or other embodiments herein.

Reference is now made to FIG. 5, which illustrates an alternative embodiment of an access sleeve 250 that may be used instead of the sleeve 200 of FIGS. 4a-4b. The sleeve 250 includes some of the features of the sleeve 200, such as being of generally cylindrical configuration and extending in a longitudinal direction. The sleeve 250, however, is sized such that the bone anchor 102 and fastening member 104 may slide through the volume of the sleeve (i.e., there is no engagement portion for removably engaging the fastening member 104). The sleeve 250 may also include a slot 266 extending from one end 254a to another end 254b. In some embodiments, the slot 266 need not extend all the way to ends 254a and/or 254b. The slot 256 is preferably operable to permit the end portions 110a, 110b of the rod 106 to pass therethrough such that the sleeve 250 may assist in guiding the rod 106 into position for fixing to the bone anchors 102. The slot 216 is also in communication with the second end 254b of the sleeve 250 such that the sleeves 250 may be removed from the patient without disturbing the position of the rod 106 with respect to the bone anchors 102. In use, the sleeve 250 may be placed in the stub incision before the bone anchor 102 is inserted through the incision. Thus, the sleeve 250 provides access to the implantation cite with minimal impact to the muscle of the patient. Those skilled in the art will appreciate that some of the aforementioned steps for the implantation procedure may be applied in a surgery using sleeves 250.

Figure 6:
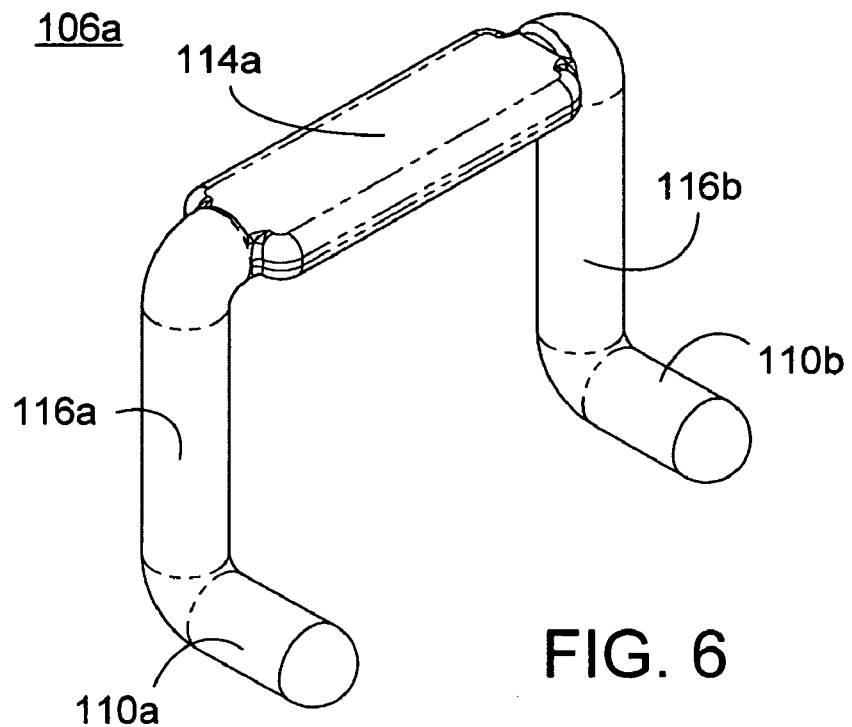
FIG. 6 is a perspective view of an alternative rod embodiment suitable for use with the bone stabilizer system of FIG. 1 and/or one or more other embodiments of the present invention.

Reference is now made to FIG. 6, which illustrates an alternative embodiment of the rod 106a. In this embodiment, the connecting portion 114a may be flattened, in order to further reduce potential trauma, particularly to smooth muscle layers and/or to the fat and/or skin. As the connecting portion 114a may lie substantially atop the muscle but under skin and fat tissue, the flattened connecting portion 114a may also advantageously affect not only the potential trauma to muscles, but al-so may enhance efficacy by providing a smooth outer appearance post-surgically.

Figure 7:
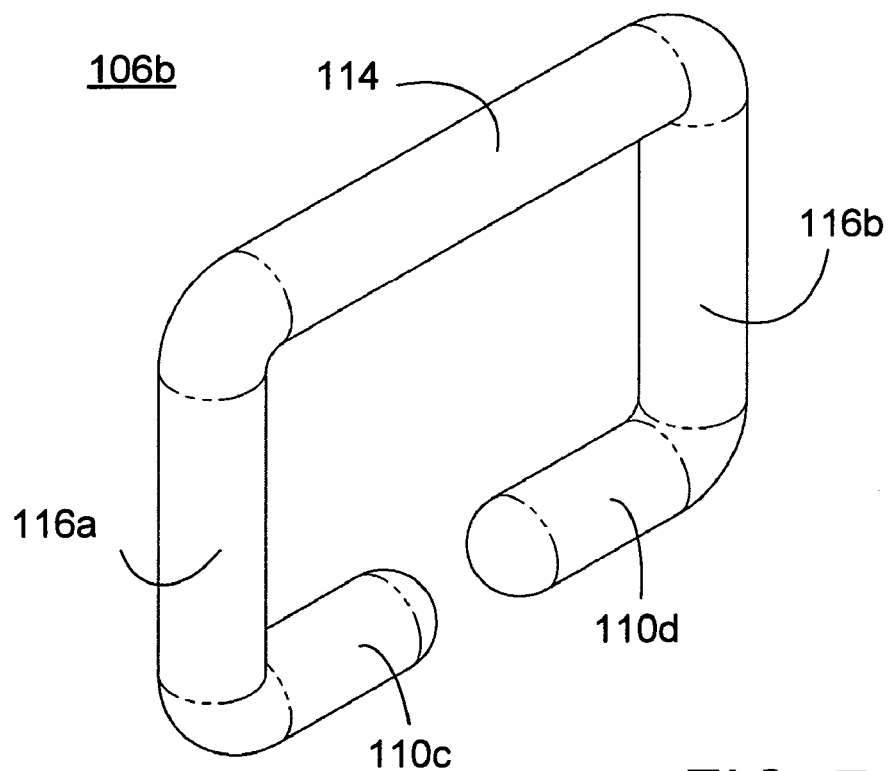
FIG. 7 is a perspective view of a further alternative rod embodiment suitable for use with the bone stabilizer system of FIG. 1 and/or one or more other embodiments of the present invention.

Reference is now made to FIG. 7, which illustrates a further alternative design of the rod 106b having analogous features to the rod 106 of FIG. 2. In this embodiment, however, the end portions 110c, 110d of the rod 106b are oriented in respective receiving directions (e.g., for the fastening members 104) that are substantially axially aligned and extend in substantially opposite directions such that end portion 110c extends substantially towards end portion 110d. This type of rod 106b may be particularly useful in situations where the space between the fastening members 104 is relatively small, such as in the area of the L5-S1 vertebrae. When using rod 106b, the first and second transverse portions 116a, 116b extend from the end portions 110a, 110b, respectively, so as to increase distance between the transverse portions 116a, 116b even though the fastening members 104 may be quite close to one another. Again, the connecting portion 114 of the rod 106b may lie superficially with respect to the muscle and/or other anatomical structures.

Figure 8:
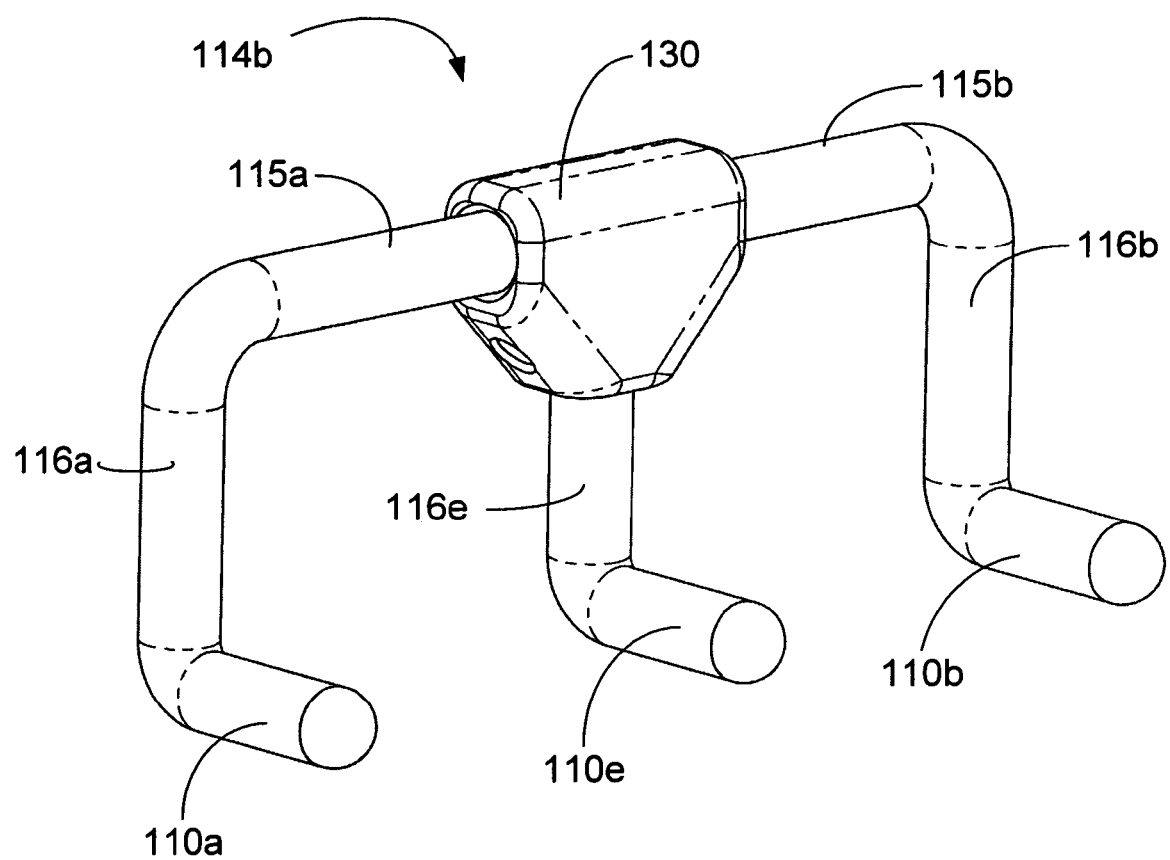
FIG. 8 is a perspective view of an alternative rod embodiment suitable for use in a multi-level stabilization application in accordance with one or more embodiments of the present invention.
Figure 9:
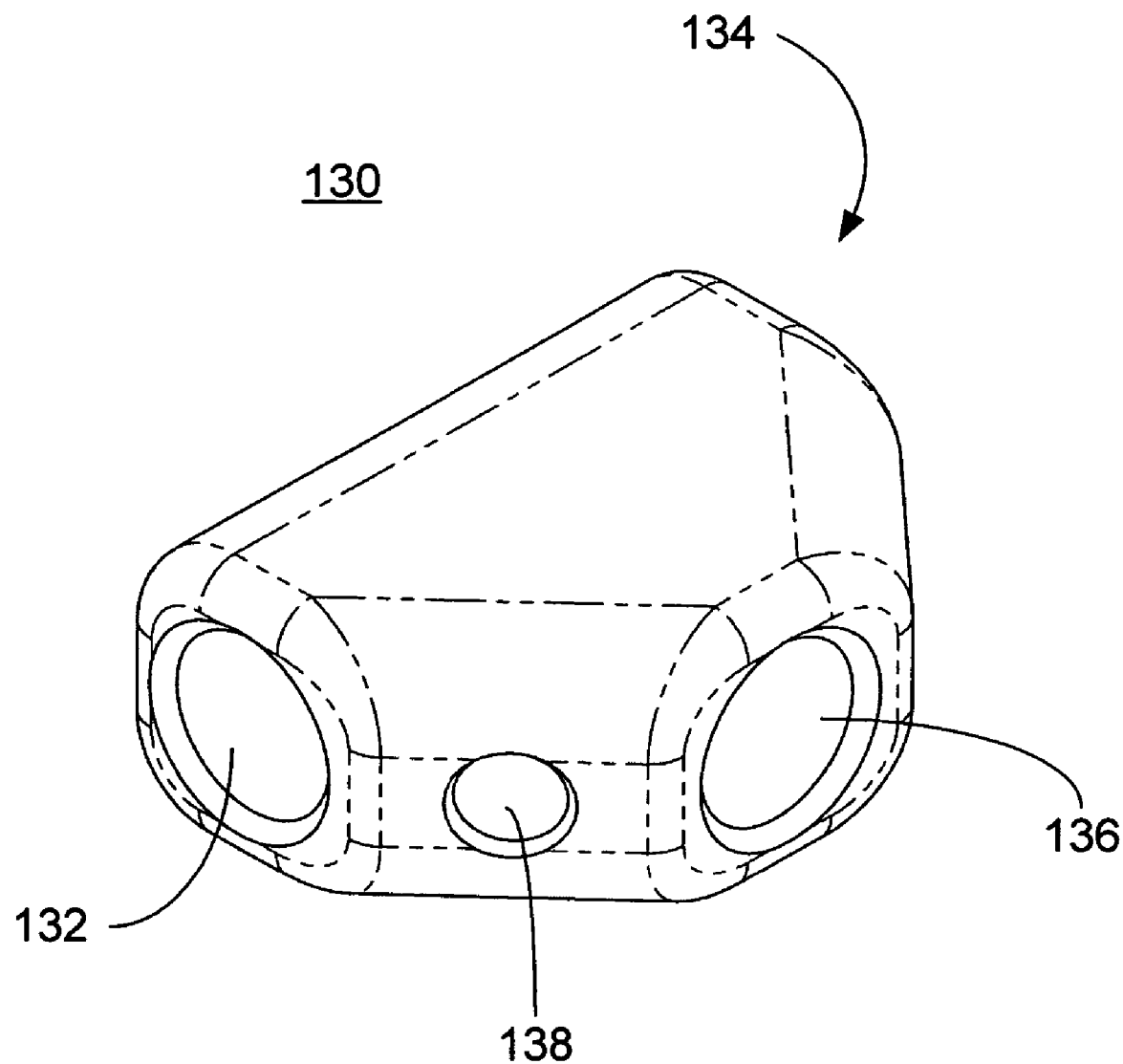
FIG. 9 is a perspective view of a coupling suitable for use with the rod assembly of FIG. 8 and/or one or more other embodiments of the present invention.

Reference is now made to FIGS. 8-9, which illustrate a rod 106c suitable for multi-level stabilization. Indeed, there may be a need to stabilize three adjacent vertebrae (or other types of bones). To address such a need, the rod 106c includes a first end portion 110a, a first transverse portion 116a extending transversely from the first end portion 110a, a second end portion 110b, a second transverse portion 116b extending transversely from the second end portion 110b, a third end portion 110e, and a third transverse portion 116e extending transversely from the third end portion 110e. The rod 106c also includes and a connecting portion 114b extending in a longitudinal direction to each of the first, second, and third transverse portions 116a, 116b, 116e.

The rod 106c is operable for use with at least first, second and third bone anchors 102 (not shown), of substantially the same properties and variations as discussed above with respect to other embodiments of the invention. Each bone anchor 102 may be disposed in a respective bone or portion of a bone to facilitate multi-level stabilization.

The rod 106c further includes a coupling 130 for interconnecting the third transverse portion 116e to the connecting portion 114b. Preferably, the third transverse portion 116e is disposed between the first and second transverse portions 116a, 116b, although other configurations are contemplated as will be apparent to those skilled in the art from the description herein. In one or more embodiments, the connecting portion 114b is continuous and the coupling 130 may slide along the connecting portion 114b to a desirable position to accommodate the particular anatomy of the patient. In an alternative embodiment, the connecting portion 114b may include at least first and second separate lengths 115a, 115b connected together by way of the coupling 130. The first length 115a is connected at an end thereof to the first transverse portion 116a, and the second length 115b of the connecting portion 114b is connected at an end thereof to the second transverse portion 116b.

The coupling 130 is operable to receive and fixedly connect the respective ends of the first and second lengths 115a, 115b of the connecting portion 114b, and the third transverse portion 116e. The coupling 130 may include at least first and second axially aligned bores 132, 134, each for receiving the connecting portion 114b (whether of continuous construction or having first and second lengths 115a, 115b). The coupling 130 may further include at least a third bore 136 transverse to the first and second bores 132, 134, for receiving the third transverse portion 116e. The coupling 130 may also include access openings 138 through which tightening screws or apparatus (not depicted) may be manipulated to affix the transverse portion 116e and the lengths 115a, 115b in place.

It is noted that the rod 106b may be further modified to include four, five, or even more additional transverse and end portions to facilitate further levels of stabilization. It is further envisioned that these additional transverse and end portions may be connected via a modified joint member or by additional individual joint members 130.

In an alternative embodiment, the coupling 130 may be used as shown (and preferably without the third bore 136) to interconnect respective lengths of a connecting portion of a stabilization rod in a single level application. The stabilization rod may be configured in substantially the same ways as in any of the single level embodiments herein, however, the connecting portion thereof would be separated (e.g., bisected), such that respective lengths are obtained. The first and second axially aligned bores 132, 134 may then receive and fix the respective lengths of the connecting portion of the stabilization rod.

Figure 10:
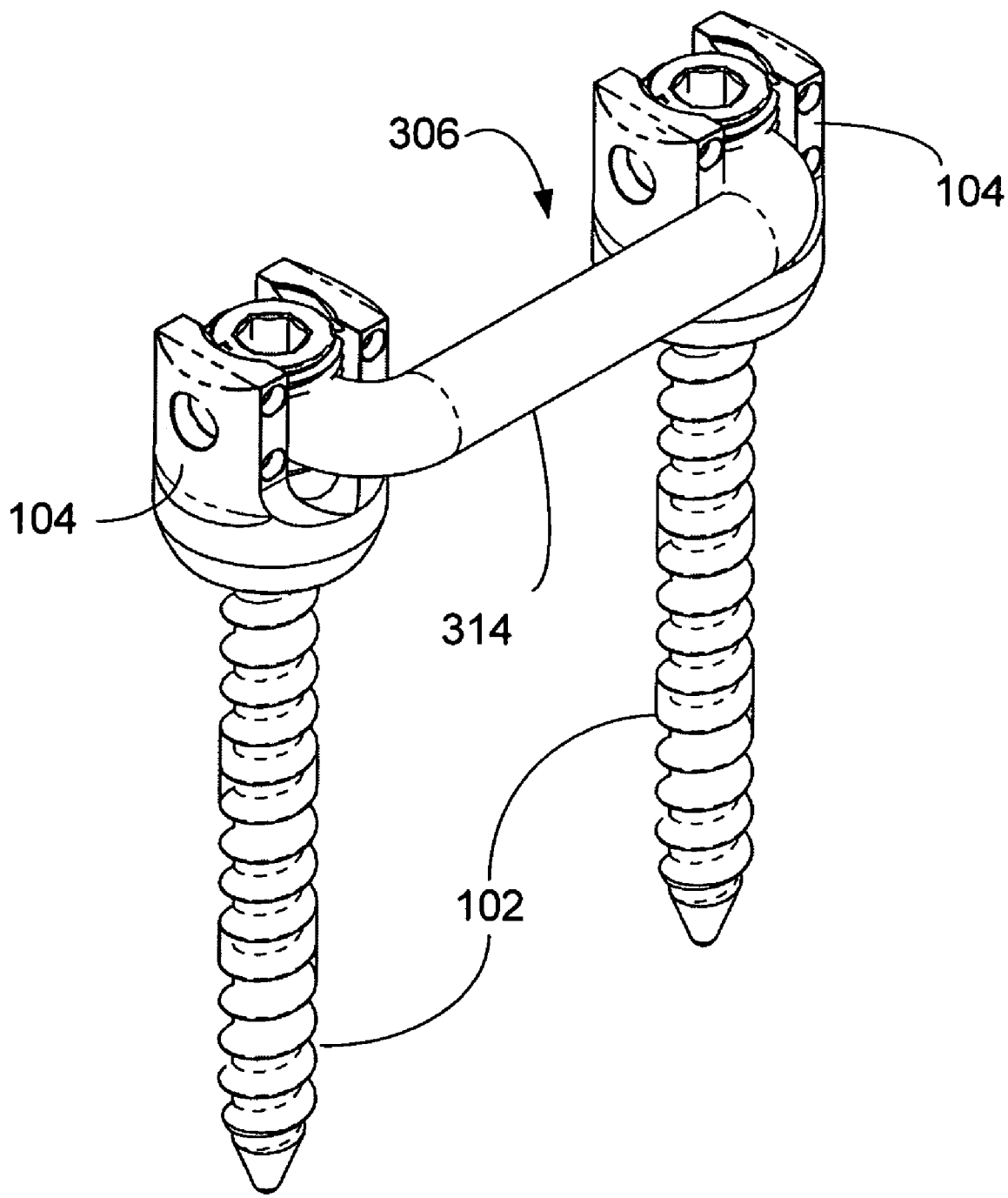
FIG. 10 is a perspective view of an alternative bone stabilizer system in accordance with one or more further embodiments of the present invention.

Reference is now made to FIG. 10, which is a perspective view of a bone stabilizer system 300 in accordance with an alternative embodiment of the invention. The stabilization system 300 includes the aforementioned bone anchors 102 (and/or variants) and a rod 306. The rod 306 differs from the rod 106 illustrated in FIG. 2, at least in that the rod 306 does not include the transverse portions 116a, 116b. The rod 106 includes end portions 310a, 310b, and a longitudinal connection portion 314. Some clearance from the fastening members 104 may be provided by the end portions 310a, 310b, which generally extend transversely from the connection portion 314 to the respective fastening members 104.

In this embodiment, receiving directions of the fastening members 104 are oriented substantially parallel to one another, and the end portions 310a, 310b of the rod 306 are likewise oriented. Thus, the system 300 is particularly useful when the given parallel orientation is necessary or desired, such as when there is some obstruction (e.g., a pedicle, or other anatomical structure) between the fastening members 104. In such an instance, the connecting portion 314 may avoid the obstruction with appropriate selection of the respective lengths of the end portions 310a, 310b.

When the rod 306 is fixed to the respective fastening members 104, the fastening members 104 are operable to receive and fix the end portions 310a, 310b in the respective insertion directions, which are transverse to the longitudinal direction of the connecting portion 314 and the bone insertion directions. The respective insertion directions of the fastening members 104 (and the end portions 310a, 310b) are substantially not axially aligned. For example, the respective insertion directions are substantially parallel to one another.

In the system 300, the respective bone anchors 102 lay substantially in a first plane. The orientation of the end portions 310a, 310b of the rod 306 and the orientation of the receiving directions of the fastening members 104 are operable to position the connecting portion 314 in a laterally offset position from the first plane. Indeed, the orientation of the end portions 310a, 310b of the rod 306 and the orientation of the receiving directions of the fastening members 104 are operable to orient the end portions 310a, 310b and the connecting portion 314 in a second plane that is substantially transverse to the first plane. This effectively takes the connecting portion 314 of the rod 306 out of axial alignment with the fastening members 104, which as discussed above may be advantageous for avoiding anatomical structures between the bone anchors 102.

In one or more embodiments of the invention, the stabilizing system 300 may be used with a coupling that provides an additional end portion 310 to allow multi-level stabilization. Those skilled in the art will appreciate that the rod 306 and an appropriate coupling may be fashioned (e.g., by modifying the coupling 130 of FIG. 9) to achieve multi-level stabilization using the system 300. Additional couplings and end portions may be further employed to stabilize additional levels of bone.

It is noted that the sleeves 200, 250 discussed hereinabove may be employed to assist in the implantation of the system 300. As it is believed that the description of the sleeves 200, 250 is sufficiently detailed to enable one skilled in the art to understand how to practice the use of the sleeves 200, 250 with the system 300, such details will not be reiterated or otherwise set forth here.

Figure 11A:
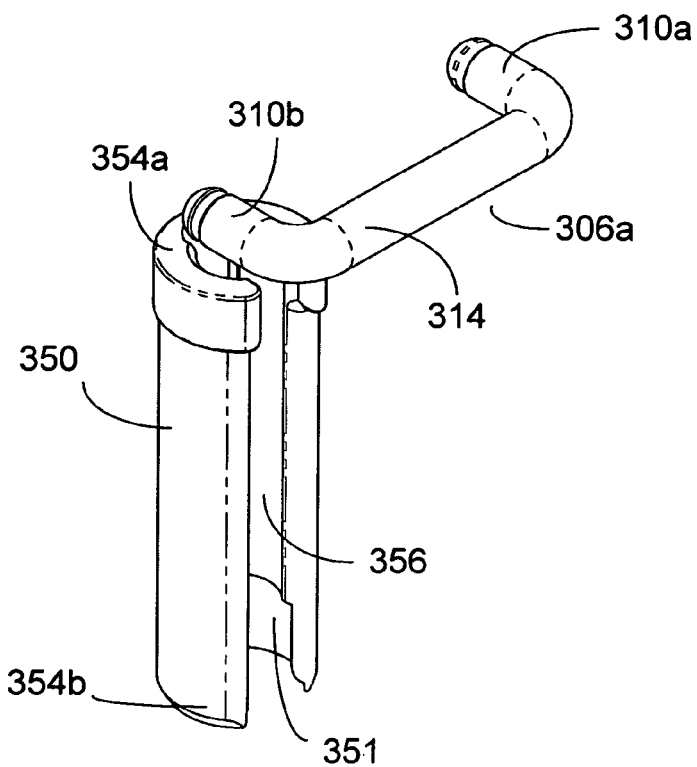
FIGS. 11a and 11b are perspective and top views, respectively, of a sleeve and alternative rod design for the bone stabilizer system of FIG. 10 and/or other embodiments herein.
Figure 11B:
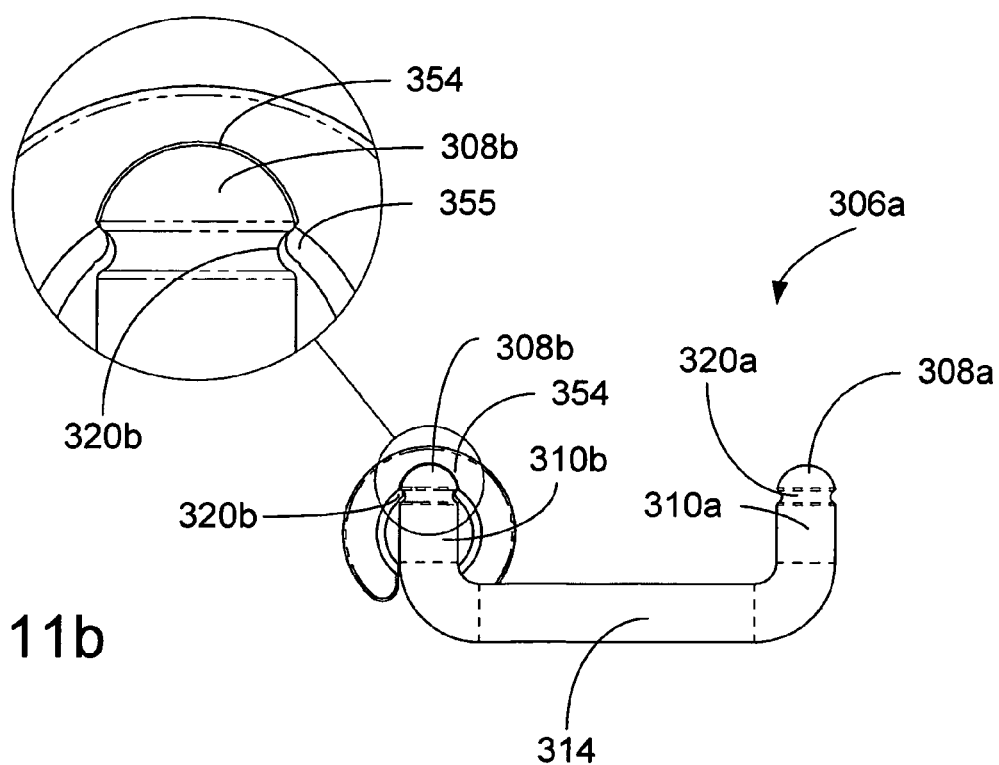

With reference to FIGS. 11a, 11b, an alternative sleeve 350 is depicted. The sleeve 350 is similar to the sleeve 200 discussed above. The sleeve 350 includes an engagement portion 310 for removably engaging the fastening members 104. As with the sleeve 200, the sleeve 300 also includes a slot 356 and a channel 354 that extend from one end 354a to another end 354b of the sleeve 350, it being understood that in some embodiments the slot 356 and/or channel 354 need not extend all the way to ends 354a and/or 354b. The channel 354 may be contoured to conform to the terminal end 308 of the rod 306a. (As will be discussed below, the rod 306a is a modified version of the rod 306 of FIG. 10.)

The channel contour and the end portions 310a, 310b of the rod 306a are keyed such that the end portions 310a, 310b may enter and slide in the channel 354 along its length but may not be disengaged in a transverse direction from the channel 354. This functionality addresses a potential problem that may arise during the implantation procedure: where undesirable slipping of the rod 306a relative to the sleeve 350 during placement of the rod 306a and subsequent movement into its final position. Indeed, the anatomy of the patient may cause the sleeves 350 to be somewhat anti-parallel (but generally directed away from the bone insertion directions). Without taking corrective measures, the anti-parallel orientation of the sleeves 350 may tend to urge the rod 306a out of the slots 356 and otherwise hinder the progression of the rod 306a to the fastening members 104. By way of example, the channel contour may include at least one undercut groove 355 (providing at least one lip) at least partially along the length thereof. The end portions 310a, 310b of the rod 306a may include corresponding grooves 320a, 320b, respectively. For example, the corresponding grooves 320a, 320b, may be at least partially circumferential grooves. For purposes of discussion the grooves 320a, 320b, are illustrated and described herein as fully circumferential grooves. The undercut groove 355 and the circumferential grooves 320a, 320b may be sized and shaped such that the end portions 310a, 310b may enter and slide in the channel 354 but may not be disengaged in a transverse direction from the channel 354. As will be discussed below, this capture feature is helpful in preventing the rod 306a from popping out of the slot 356 as the surgeon slides the rod 306a toward its ultimate position in the fastening members 104.

By way of example, a procedure for implanting the stabilization system 300 into a patient will now be described. At least one (and preferably a single) incision is made over the respective bones or bone portions to be stabilized. The incision is longitudinally disposed with respect to the longitudinal direction of the connecting portion 314 of the spine of the patient. The incision may then be dilated. The skin, fat, and muscle layers are preferably peeled back to expose the bone surfaces to be stabilized. This process notably differs from that of the earlier described surgical embodiment, at least in that the muscle tissue is directly incised and/or otherwise disturbed substantially along the axis between the bone anchors 102.

The bone anchors 102 may be inserted into the incision at the desired anchoring positions. If desired, one or more of the sleeves 200, 250, and/or 350 may be employed to assist in the implantation. In this example, the sleeves 350 are contemplated and, when the bone anchors 102 are fixed to the bone, extend at or above the skin. The sleeves 350 are placed with their respective slots 356 oriented to match the orientation of the end portions 310a, 310b of the rod 306a, thereby also preferably orienting the fastening members 104 of the bone anchors 104. The respective bone anchors 102 are fixed to the respective bone(s), and the fastening members 104, if articulable, are articulated to an orientation providing receiving directions oriented to match the orientation of the end portions 310a, 310b of the rod 306a.

As noted above, the anatomy of the patient may cause the sleeves 350 to be somewhat anti-parallel (but generally directed away from the bone insertion directions). The surgeon may use the slots 356 and/or channels 354 of the sleeves 350 to assist in aligning the sleeves 350 (and fastening members 104) to more easily receive the rod 306a. The capture feature of the channel 354 (via the keyed contours of the channel and the rod) assists in preventing undesirable slippage of the rod 306a from the sleeves 350. The surgeon may insert the first end portion 310a of the rod 306a through the slot 356 of a first sleeve 350 such that the end portion 310a enters and slides in the channel 354 of the sleeve 350 along its length toward the fastening member 104 of the bone anchor 102. Notably, once the circumferential groove 320a of the rod 306a engages the channel 354, the end portion 310a of the rod 306a may not slip out of the slot 356 transversely. Then the surgeon may insert the second end portion 310b of the rod 306a through the slot 356 of a second sleeve 350 such that the second end portion 310b may enter and slide in the channel 354 thereof toward the fastening member 104 of the bone anchor 102. Again, once the circumferential groove 320b of the rod 306a engages the channel 354, the end portion 310b of the rod 306a may not slip out of the slot 356 transversely.

The insertion of the first and second end portions 310a, 310b of the rod 306a into the sleeves 350 thus urges the fastening members 104 into articulation positions suitable for receiving and fixing the rod 306a thereto. The surgeon may slide the rod 306a along the slots 356 toward the fastening members 104 of the bone anchors 102, and fix the first and second end portions 310a, 310b thereof to the respective fastening members 104. The channel contour communicates with the second end 354b of the access sleeve 350 such that the sleeve may be removed from the fastening member 104 after the end portion 310 of the rod 306a has been fixed to the fastening member 104. The surgeon may then close the incision.

It is noted that the various rod embodiments herein exhibit a desirable feature, which may be useful in treating one or more abnormal curvatures of the spine, such as abnormal kyphotic, abnormal lordotic, or scoliotic curvatures. Kyphotic curvature typically refers to the outward curve of the thoracic spine (at the level of the ribs). Lordotic curvature generally refers to the inward curve of the lumbar spine (just above the buttocks). Scoliotic curvature is a sideways curvature of the spine and is always abnormal. While a small degree of both kyphotic and lordotic curvature is normal, exaggeration of the kyphotic curve is described as round shoulders or hunched shoulders (the medical term is Scheuermann's disease). Exaggeration of the lordotic curve is often called swayback (the medical term is lordosis).

One or more of the stabilization rods herein include the respective first and second end portions, each extending in respective directions (transverse to the connecting portion) for entering respective fastening members 104 of the bone anchors 102. The respective directions of the first and second end portions may be oriented such that, when implanted, the receiving directions of the fastening members 104 are laterally oriented with respect to the patient's spine. Thus, the transverse orientation of the first and second end portions and the length of the connecting portion, when implanted, may influence a distance between the respective fastening members 104 of the bone anchors 102. This may be useful in adjusting the respective vertebral bones of the patient to adjust one or more of the aforementioned kyphotic, lordotic, or scoliotic curvatures.

For example, depending on the positioning of the bone anchors 102 and the orientation of the receiving directions of the fastening members 104, the transverse orientation of the first and second end portions may be operable as respective hooks to draw the respective fastening members 104 of the bone anchors 102 toward one another when implanted. Alternatively, the first and second end portions may be operable as respective displacement elements to push the respective fastening members 104 of the bone anchors 102 away from one another when implanted.

FIGS. 12a-e illustrate various embodiments of rods suitable for use in connection with the stabilization systems of the present invention. It is understood that the embodiments illustrated do not represent a complete set of the rods suitable for use with the invention; rather, they are provided by way of example only.

Figure 12A:
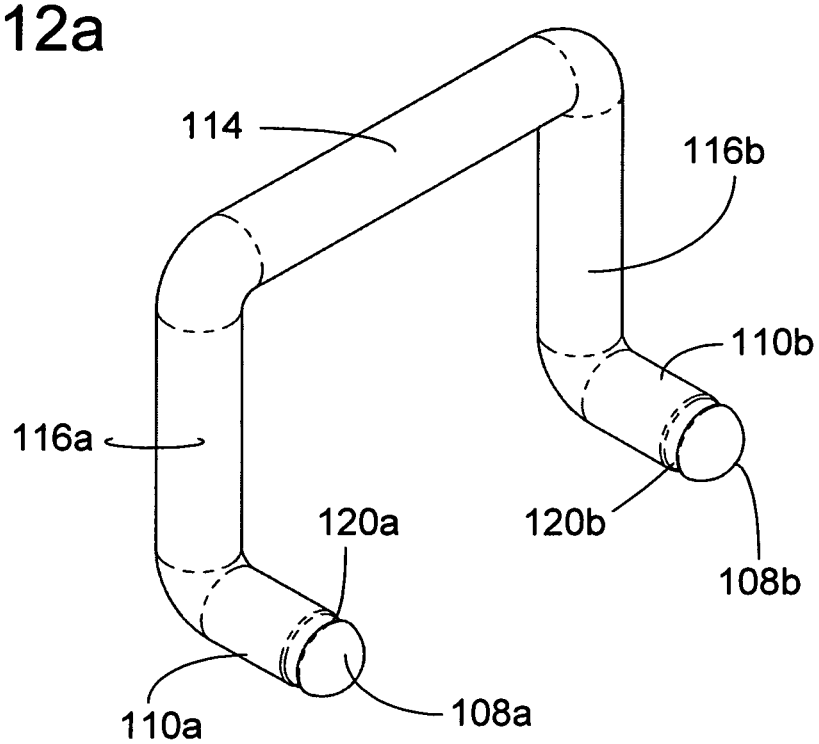
FIGS. 12a-12e are perspective views of exemplary rods of a bone stabilizer system in accordance with one or more embodiments of the present invention.

FIG. 12a depicts a rod 106d that shares many of the same features as the rod 106 of FIG. 2. In this embodiment, however, the rod 106d includes grooves 120a, 120b (for example, at least partially circumferential grooves) at the end portions 110a, 110b. Thus, the rod 106d is well suited for use in connection with the sleeve 350, although the other sleeves may also be used.

Figure 12B:
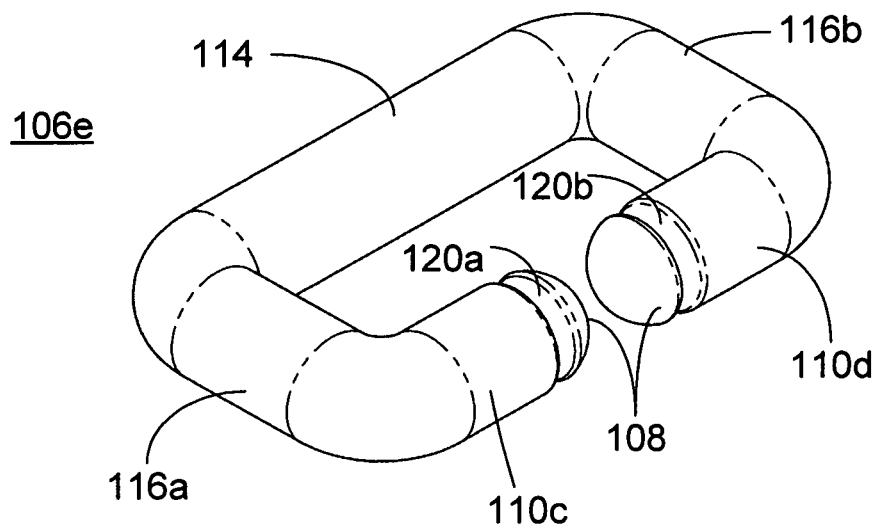

FIG. 12b depicts a rod 106e that is substantially similar to the rod 106b of FIG. 7, which may be used, for example, when the fastening members 104 are located close to each other (e.g., in vertebral stabilization applications in the L1-S5 area). In this embodiment, the rod 106e features end portions 110c, 110d having, e.g., at least partially circumferential, grooves 120a, 120b for engaging corresponding keyed portions of the sleeves 350.

Figure 12C:
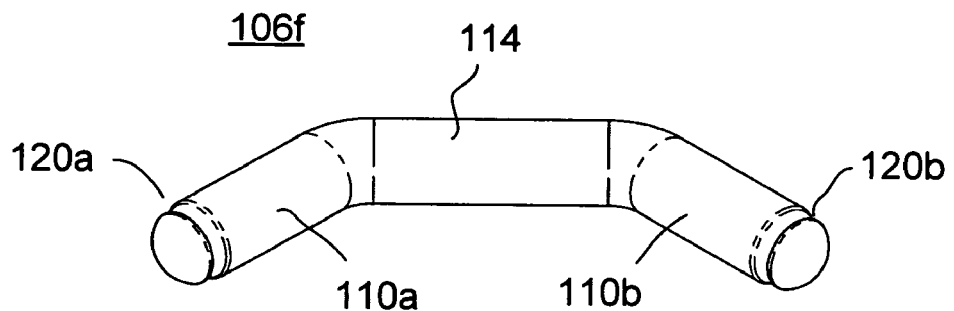

FIG. 12c depicts a rod 106f generally most advantageously used when the fastening members 104 do not provide receiving directions oriented substantially axially aligned with, or parallel to, one another, and yet the anatomy of the patient indicates that an offset of the connecting portion 114 (from the axis through the fastening members 104) would be desirable. This type of situation might arise, for example, where some obstruction lies between the fastening member 104, but the obstruction is not easily or advisably removed. The end portions 110a, 110b extend from the connecting portion 114 at an obtuse angle. The joint where the end portions 110a, 110b meet the connecting portion 114 may be angular or rounded. Although not required, the end portions 110a, 110b may include grooves 120a, 120b (such as at least partially circumferential grooves).

Figure 12D:
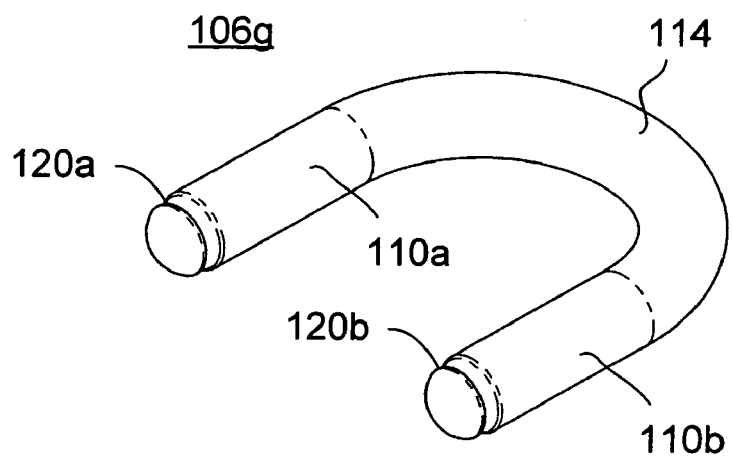

FIG. 12d depicts a rod 106g in which the joint between the connecting portion 114 and the end portions 110a, 110b is substantially rounded, such that the rod 106g appears as a substantially smoothly bent structure, giving the overall rod 106g a smooth "U" shape.

Figure 12E:
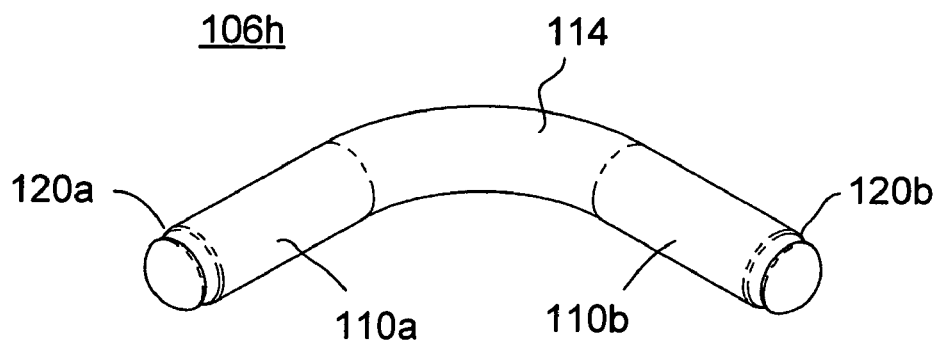

FIG. 12e depicts a rod 106h in which the joint between the connecting portion 114 and the end portions 110a, 110b is also substantially rounded, (although at a shallower angle as compared with the rod 106g of FIG. 12d).

It is preferred that the rods, fastening members, bone anchors, etc. be formed from biologically acceptable materials, such as titanium, titanium alloy, cobalt chromium alloy, stainless steel, plastics, etc., although it is preferred that the material is highly polished so that it does not irritate the patient's soft tissue.

Some additional notable features of the aforementioned systems are listed below, it being understood that various features alone or in combination may be employed:

One or more of the rods may be pre-formed and made from highly-rigid materials to work with pedicle screw systems that require only skin incisions.

One or more of the rod may be adapted to include a coupling that is movable to accommodate multi-level applications.

Certain of the exemplary systems allow the avoidance of longitudinal incisions in muscle tissue, which helps to avoid significant muscle trauma.

The connecting portion of the rod may be designed to reside above the muscle to limit muscle incision.

Advantageously, the systems and methods discussed hereinabove represents a significant reduction in the amount of trauma to the patient particularly with respect to the muscle in and around the vertebrae at issue.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An access sleeve for use in implanting a stabilization system into a patient, comprising:
    an exterior surface;
    first and second spaced apart ends, the second end being operatively connectable to a rod fastening member of a bone anchor;
    an interior surface defining a volume;
    a slot extending at least partially along a length of the exterior surface of the access sleeve and providing an opening into the volume; and
    a channel extending along a length of the interior surface, being disposed substantially opposite to the slot, and including a contour complementing a contour of an end of an interconnecting rod, the end portion of the rod including a groove, the channel contour being such that the end portion of the rod may enter and slide in the channel along its length toward the rod fastening member of the bone anchor, an the channel contour including at least one undercut groove at least partially along the length thereof, wherein:
    the contour of the channel includes at least one undercut groove providing at least one lip at least partially along the length thereof such that a rod disposed in the slot is prevented from dislocating out of the slot,
    the slot is sized and shaped such that an end portion of the rod passes therethrough, and slides along the length of the access sleeve toward the second end thereof and toward the rod fastening member of the bone anchor such that the access sleeve assists in guiding the rod into positioning for fixing to the bone anchor, and
    the undercut groove and the groove of the rod are sized and shaped such that the end portion may enter and slide in the channel along its length but may not be disengaged in a transverse direction from the channel.

2. The access sleeve of claim 1, wherein the channel contour and the end portion of the rod are keyed such that the end portion may enter and slide in the channel along its length but may not be disengaged in a transverse direction from the channel.

3. The access sleeve of claim 1, wherein the groove of the rod extends at least partially circumferentially about the end thereof.

4. The access sleeve of claim 1, wherein the channel contour communicates with the second end of the access sleeve such that the sleeve may be removed from the rod fastening member after the rod has been fixed to the rod fastening member.

5. The access sleeve of claim 1, wherein the second end of the access sleeve is sized and shaped to friction fit to the fastening member of the bone anchor.

6. The access sleeve of claim 1, wherein a length of the sleeve is defined between the first and second spaced apart ends thereof, and the sleeve is operable such that the length may be adjusted by cutting the sleeve to produce a new first end thereof.

7. An apparatus, comprising:
    at least one bone anchor including a shaft extending in a bone insertion direction for connection to a respective bone of a patient, and a fastening member; and
    an access sleeve for use in guiding an elongate member into the fastening member during implantation, the access sleeve including: an exterior surface, first and second spaced apart ends, the second end being operatively connected to the fastening member of the bone anchor, an interior surface defining a volume, a slot extending at least partially along a length of the exterior surface of the access sleeve and providing an opening into the volume, and a channel extending along a length of the interior surface, being disposed substantially opposite to the slot, and including a contour complementing a contour of an end of the elongate member, wherein:
    the contour of the channel includes at least one undercut groove, at least partially along the length thereof, providing at least one lip such that a rod, having an end portion including a groove, disposed in the slot is prevented from dislocating out of the slot, and the channel contour is such that the end portion of the rod may enter and slide in the channel along its length toward the fastening member of the at least one bone anchor, and
    the slot is sized and shaped such that the end portion of the rod passes therethrough, and slides along the length of the access sleeve toward the second end thereof and toward the fastening member of the at least one bone anchor such that the access sleeve assists in guiding the rod into positioning for fixing to the at least one bone anchor, wherein:
    the undercut groove and the groove of the rod are sized and shaped such that the end portion may enter and slide in the channel along its length but may not be disengaged in a transverse direction from the channel.

8. The apparatus of claim 7, wherein the second end of the access sleeve is sized and shaped to friction fit to the fastening member of the bone anchor.

9. The access sleeve of claim 7, wherein a length of the sleeve is defined between the first and second spaced apart ends thereof, and the sleeve is operable such that the length may be adjusted by cutting the sleeve to produce a new first end thereof.

10. A stabilization rod for implantation in a patient, comprising:
   first, second, and third end portions, each extending in respective insertion directions for entering respective fastening members of respective bone anchors in respective receiving directions;
   a connecting portion extending between the first and second end portions in a longitudinal direction transverse to the respective insertion directions;
   first, second, and third transverse portions extending transversely from the first, second, and third end portions, respectively to respective ends of the connecting portion; and
   a coupling for interconnecting the third transverse portion to the connecting portion, the coupling including at least first and second axially aligned bores, each for receiving the connecting portion of the elongate member; and at least a third bore transverse to the first and second bores, for receiving the third transverse portion,
   wherein the respective receiving directions extend in substantially opposite directions, the first end portion extends substantially towards the second end portion, the connecting portion extends to each of the first, second, and third transverse portions; and at least one of:
   the connecting portion is a continuous member and the coupling is operable to slide thereon to different positions; and the connecting portion includes at least first and second lengths, the first length of the connecting portion being connected at a first end thereof to the first transverse portion and the second length of the connecting portion being connected at a first end thereof to the second transverse portion, and the coupling is operable to receive and fixedly connect the respective second ends of the first and second lengths of the connecting portion, and the third transverse portion.

11. The stabilization rod of claim 10, wherein the respective insertion directions of the first and second end portions are substantially parallel with one another.

12. The stabilization rod of claim 10, wherein the respective insertion directions of the first and second end portions are oriented such that the receiving directions of the fastening members are transverse to the longitudinal direction of the connecting portion.

13. The stabilization rod of claim 10, wherein the respective insertion directions of the first and second end portions are oriented such that, when implanted, the receiving directions of the fastening members are laterally oriented with respect to the patient's spine.

14. The stabilization rod of claim 10, wherein the transverse orientation of the first and second end portions and a length of the connecting portion, when implanted, influence a distance between the respective fastening members of the bone anchors.

15. The stabilization rod of claim 14, wherein the transverse orientation of the first and second end portions with respect to the length of the connecting portion are operable as respective hooks to draw the respective fastening members of the bone anchors toward one another when implanted.

16. The stabilization rod of claim 14, wherein the transverse orientation of the first and second end portions with respect to the length of the connecting portion are operable as respective displacement elements to push the respective fastening members of the bone anchors away from one another when implanted.

17. The stabilization rod of claim 10, wherein the third transverse portion is disposed between the first and second transverse portions.

18. A stabilization system for implantation in a patient, comprising:
   at least first and second bone anchors, each bone anchor including a shaft extending in a respective bone insertion direction for connection to a respective bone of a patient, and a fastening member;
   an elongate member comprising a first end portion including a groove disposed at an end of the first end portion thereof, a first transverse portion extending transversely from the first end portion, a second end portion, a second transverse portion extending transversely from the second end portion, and a connecting portion extending in a longitudinal direction between the first and second transverse portions; and
   at least one access sleeve including: an exterior surface; first and second spaced apart ends, the second end being operatively connectable to the fastening member of a given one of the bone anchors; an interior surface defining a volume; a slot extending at least partially along a length of the exterior surface of the access sleeve and providing an opening into the volume, the slot being sized and shaped to receive the first end portion of the elongate member such that the first end portion may slide along the length of the access sleeve toward the second end thereof and toward the fastening member of the given bone anchor; and a channel extending along a length of the interior surface, being disposed substantially opposite to the slot, and including a contour complementing a contour of at least one of the first and second end portions of the elongate member, the channel contour being such that the first end portion of the elongate member may enter and slide in the respective channel along its length toward the fastening member of the bone anchor, and the channel contour including at least one undercut groove at least partially along the length thereof, wherein:
   (i) the channel contour and at least the first end portion of the elongate member are keyed such that the first end portion may enter and slide in the channel along its length but may not be disengaged in a transverse direction from the channel;
   (ii) the undercut groove and the groove of the elongate member are sized and shaped such that the first end portion may enter and slide in the channel along its length but may not be disengaged in a transverse direction from the channel; and
   (iii) the connecting portion is laterally offset from a first plane substantially through the at least first and second bone anchors.

19. The stabilization system of claim 18, wherein the respective fastening members are operable to receive and fix at least one of the first and second end portions in respective receiving directions, which are transverse to the bone insertion direction.

20. The stabilization system of claim 19, wherein the respective receiving directions of the fastening members are substantially axially aligned and extend in substantially opposite directions.

21. The stabilization system of claim 20, wherein the first and second end portions of the elongate member are in substantial axial alignment, and the first and second transverse portions extend from the first and second end portions, respectively, so as to maximize a distance between the first and second transverse portions.

22. The stabilization system of claim 18, wherein the respective fastening members are operable to receive and fix at least one of the first and second end portions in respective receiving directions, which are transverse to the longitudinal direction.

23. The stabilization system of claim 18, wherein the first and second transverse portions are operable to position the connecting portion superfascially.

24. The stabilization system of claim 18, wherein the first and second transverse portions are operable to position the connecting portion, when implanted, a predetermined distance away from the fastening members of the bone anchors.

25. The stabilization system of claim 24, wherein the predetermined distance is about a thickness of muscle tissue proximate to the bone anchors.

26. The stabilization system of claim 25, wherein the muscle tissue of the patient is posterior to the patient's spine.

27. The stabilization system of claim 18, wherein the first and second transverse portions are operable to offset the connecting portion with respect to the fastening members in a direction at least partially opposite the respective bone insertion directions.

28. The stabilization system of claim 27, wherein:
the first and second end portions lay substantially in a second plane; and
the first and second transverse portions lay substantially in a third plane, transverse to the second plane.

29. The stabilization system of claim 28, wherein the second and third planes are substantially perpendicular with respect to one another.

30. The stabilization system of claim 28, wherein the connecting portion lies and the first and second transverse portions lay substantially in the third plane.

31. The stabilization system of claim 28, wherein the shafts of the bone anchors lay substantially in the first plane, which is transverse with respect to the second plane.

32. The stabilization system of claim 18, wherein the respective receiving directions of the fastening members are not substantially axially aligned.

33. The stabilization system of claim 32, wherein the shafts of the bone anchors lay substantially in the first plane and the respective receiving directions of the fastening members are substantially transverse to the first plane.

34. The stabilization system of claim 33, wherein the respective receiving directions are offset in correspondence with the coupling portion of the elongate member, and are in substantially parallel alignment.

35. The stabilization system of claim 18, wherein the first and second end portions of the elongate member are not substantially axially aligned and lie substantially in a second plane, and the first and second transverse portions lie substantially in a third plane transverse to the second plane.

36. The stabilization system of claim 18, wherein the elongated member further comprises a groove disposed at an end of at least one of the first and second end portions thereof.

37. The stabilization system of claim 36, wherein the groove extends at least partially circumferentially about the end.

38. The stabilization system of claim 18, wherein the connecting portion includes a substantially flattened cross-section for reduction of interference with tissue of the patient.

39. The stabilization system of claim 18, wherein the groove of the elongate member extends at least partially circumferentially about the end of the first end portion.

40. The stabilization system of claim 18, wherein the channel contour communicates with the second end of the access sleeve such that the sleeve may be removed from the fastening member after the first end portion of the elongate member has been fixed to the fastening member.

41. The stabilization system of claim 18, further comprising at least two of the access sleeves, one for engagement with each of the bone anchors and for slidingly receiving a respective one of the first and second end portions of the elongate member.

42. The stabilization system of claim 41, wherein the respective slots of the access sleeves are not directed toward one another.

43. The stabilization system of claim 41, wherein the respective slots of the access sleeves are oriented such that respective receiving directions thereof are substantially parallel to one another.

44. The stabilization system of claim 18, wherein the second end of the access sleeve is sized and shaped to friction fit to the fastening member of the given one of the bone anchors.

45. A multi-level stabilization system, further comprising:
at least first, second and third bone anchors, each bone anchor including a shaft extending in a respective bone insertion direction for connection to a respective bone of a patient, and a fastening member;
an elongate member comprising a first end portion, a first transverse portion extending transversely from the first end portion, a second end portion, a second transverse portion extending transversely from the second end portion, a third end portion and a third transverse portion extending transversely from the third end portion, and a connecting portion extending in a longitudinal direction to each of the first, second, and third transverse portions; and
a coupling for interconnecting the third transverse portion to the connecting portion, the coupling including at least first and second axially aligned bores, each for receiving the connecting portion of the elongate member; and at least a third bore transverse to the first and second bores, for receiving the third transverse portion,
wherein:
the connecting portion is offset from an axis through the fastening members of the at least first and second bone anchors; and
at least one of:
the connecting portion is a continuous member and the coupling is operable to slide thereon to different positions; and
the connecting portion includes at least first and second lengths, the first length of the connecting portion being connected at a first end thereof to the first transverse portion and the second length of the connecting portion being connected at a first end thereof to the second transverse portion, and the coupling is operable to receive and fixedly connect the respective second ends of the first and second lengths of the connecting portion, and the third transverse portion.

46. The stabilization system of claim 45, wherein the respective fastening members are operable to receive and fix at least one of the first, second, and third end portions in respective receiving directions, which are transverse to the bone insertion direction.

47. The stabilization system of claim 45, wherein the respective fastening members are operable to receive and fix at least one of the first, second, and third end portions in respective receiving directions, which are transverse to the longitudinal direction.

48. The stabilization system of claim 45, wherein the third transverse portion is disposed between the first and second transverse portions.

49. The stabilization system of claim 45, wherein the first, second, and third transverse portions are operable to position the connecting portion superfascially.

50. The stabilization system of claim 45, wherein the first, second, and third transverse portions are operable to position the connecting portion, when implanted, a predetermined distance away from the fastening members of the bone anchors.

51. The stabilization system of claim 45, wherein the first, second, and third transverse portions are operable to offset the connecting portion with respect to the fastening members in a direction at least partially opposite the respective bone insertion directions.

52. The stabilization system of claim 45, further comprising one or more further transverse portions, wherein the coupling is operable to interconnect the one or more third transverse portions to the connecting portion.

53. A stabilization system for implantation in a patient, comprising: at least first and second bone anchors, each bone anchor including a shaft extending in a respective bone insertion direction for connection to a respective bone of a patient, and a fastening member;
an elongate member comprising first and second end portions, each extending in respective insertion directions, the first end portion of the elongate member including a groove disposed at an end of the first end portion thereof, and a connecting portion extending in a longitudinal direction transverse to the respective insertion directions; and
at least one access sleeve including: an exterior surface; first and second spaced apart ends, the second end being operatively connectable to the fastening member of a given one of the bone anchors; an interior surface defining a volume; a slot extending at least partially along a length of the exterior surface of the access sleeve and providing an opening into the volume, the slot being sized and shaped to receive the first end portion of the elongate member such that the first end portion may slide along the length of the access sleeve toward the second end thereof and toward the fastening member of the given bone anchor; and a channel extending along a length of the interior surface, being disposed substantially opposite to the slot, and including a contour complementing a contour of at least one of the first and second end portions of the elongate member, the channel contour being such that the first end portion of the elongate member may enter and slide in the respective channel along its length toward the fastening member of the bone anchor, and the channel contour including at least one undercut groove at least partially along the length thereof, wherein:
(i) the connecting portion is offset from an axis through the fastening members of the at least first and second bone anchors;
(ii) the channel contour and at least the first end portion of the elongate member are keyed such that the first end portion may enter and slide in the channel along its length but may not be disengaged in a transverse direction from the channel; and
(iii) the undercut groove and the groove of the elongate member are sized and shaped such that the first end portion may enter and slide in the channel along its length but may not be disengaged in a transverse direction from the channel.

54. The stabilization system of claim 53, wherein the respective fastening members are operable to receive and fix at least one of the first and second end portions in respective receiving directions, which are transverse to the bone insertion direction.

55. The stabilization system of claim 53, wherein the respective fastening members are operable to receive and fix at least one of the first and second end portions in respective receiving directions, which are transverse to the longitudinal direction.

56. The stabilization system of claim 53, wherein the connecting portion includes one or more bends such that one or more anatomical structures of the patient may be avoided.

57. The stabilization system of claim 56, wherein one or more anatomical structures of the patient are one or more facets.

58. The stabilization system of claim 53, wherein the respective insertion directions of the fastening members are substantially not axially aligned.

59. The stabilization system of claim 53, wherein the respective insertion directions of the fastening members are substantially parallel to one another.

60. The stabilization system of claim 53, wherein:
the respective bone anchors lay substantially in a first plane; and
the orientation of the first and second end portions of the elongate member and the orientation of the receiving directions are operable to position the connecting portion laterally offset from the first plane.

61. The stabilization system of claim 60, wherein the orientation of the first and second end portions of the elongate member and the orientation of the receiving directions are operable to orient the elongate member in a second plane that is substantially transverse to the first plane.

62. The stabilization system of claim 53, wherein the groove of the elongate member extends at least partially circumferentially about the end of the first end portion.

63. The stabilization system of claim 53, wherein the channel contour communicates with the second end of the access sleeve such that the sleeve may be removed from the fastening member after the first end portion of the elongate member has been fixed to the fastening member.

64. The stabilization system of claim 53, further comprising at least two of the access sleeves, one for engagement with each of the bone anchors and for slidingly receiving a respective one of the first and second end portions of the elongate member.

65. The stabilization system of claim 64, wherein the respective slots of the access sleeves are not directed toward one another.

66. The stabilization system of claim 64, wherein the respective slots of the access sleeves are oriented such that respective receiving directions thereof are substantially parallel to one another.

67. The stabilization system of claim 53, wherein the second end of the access sleeve is sized and shaped to friction fit to the fastening member of the given one of the bone anchors.

* * * * *